United States Patent [19]
Berke

[11] Patent Number: 5,984,910
[45] Date of Patent: Nov. 16, 1999

[54] URINARY INCONTINENCE DEVICE AND METHOD

[76] Inventor: Joseph J. Berke, 2063 Long Lake Shore, West Bloomfield, Mich. 48323

[21] Appl. No.: 08/978,261

[22] Filed: Nov. 25, 1997

[51] Int. Cl.⁶ .............................. A61F 5/44; A61F 5/48; A61B 19/08; A61B 17/00

[52] U.S. Cl. ...................... 604/352; 604/346; 604/385.1; 128/885; 128/854; 128/887

[58] Field of Search ................................. 128/885, 854, 128/887; 604/349, 385.1, 353, 346

[56] References Cited

U.S. PATENT DOCUMENTS

| | | | |
|---|---|---|---|
| 2,533,924 | 12/1950 | Foley | 128/885 |
| 3,364,932 | 1/1968 | Beach | 128/885 |
| 4,073,295 | 2/1978 | Laufbahn | 128/295 |
| 4,239,044 | 12/1980 | Pavlinch | 128/295 |
| 4,601,716 | 7/1986 | Smith . | |
| 4,631,061 | 12/1986 | Martin . | |
| 4,692,160 | 9/1987 | Nussbaumer . | |
| 4,702,239 | 10/1987 | Ichikawa . | |
| 4,800,900 | 1/1989 | French | 128/885 |
| 4,889,533 | 12/1989 | Beecher . | |
| 4,904,248 | 2/1990 | Vaillancourt . | |
| 4,971,074 | 11/1990 | Hrubetz | 128/885 |
| 4,994,051 | 2/1991 | Walsh | 604/349 |
| 4,997,427 | 3/1991 | Bowen | 604/349 |
| 5,004,463 | 4/1991 | Nigay . | |
| 5,037,413 | 8/1991 | Haque . | |
| 5,074,853 | 12/1991 | Bryant . | |
| 5,275,592 | 1/1994 | Grizzaffi . | |
| 5,586,978 | 12/1996 | Bayne . | |
| 5,593,389 | 1/1997 | Chang | 604/174 |
| 5,618,279 | 4/1997 | Pudlo | 604/385.1 |
| 5,645,541 | 7/1997 | Bouser | 604/353 |
| 5,727,568 | 3/1998 | Kiser | 128/885 |

FOREIGN PATENT DOCUMENTS

| | | | |
|---|---|---|---|
| 0657004 | 2/1963 | Canada | 604/349 |
| 2742298 | 3/1978 | Germany | 604/349 |
| 404114645 | 4/1992 | Japan | 604/349 |
| 8501827 | 1/1987 | United Kingdom | 604/349 |

OTHER PUBLICATIONS

URO Flow Control—Internet Printout.
ConvaTec Continence Care—Internet Printout.

*Primary Examiner*—John G. Weiss
*Assistant Examiner*—Miley C. Peppers, III

[57] ABSTRACT

An urinary incontinence device for use by a male includes an undergarment worn closely to the body and including an opening or hole through which the penis passes and is kept upright and close to the body by a flap across the opener in the undergarment. The flap may include an occlusion device integrally incorporated therein and aligned with the opening to be positioned between the base of the shaft of the penis and the scrotum to occlude the urethral passage of the penis. The occlusion device is designed to apply sufficient pressure to occlude the urethral passage without cutting off circulation of blood within the penis through the dorsal vein. The flap design maintains and retains an optimum position of the penis and occlusion of the urethral passage to prevent urine discharge in a form fitting undergarment that allows significant freedom of movement by the wearer. The occlusion device has alternative embodiments where there is no integral undergarment, such as a bands and stretchable wraps that include the occlusion device. One alternative embodiment includes an occlusion device having an adjustably expandable chamber and pump. A method for using the urinary incontinence device of the present invention is also disclosed.

19 Claims, 4 Drawing Sheets

URINARY INCONTINENCE DEVICE AND METHOD

BACKGROUND OF THE INVENTION

1. Field of the Invention

The present invention generally relates to an urinary incontinence device for use by a male to prevent urine discharge and to eliminate the necessity for any type of diaper. More particularly, the present invention is directed to a device that will maintain a position of the penis to prevent urine discharge as well as comfortably occlude the urethra of the penis to prevent urine from being uncontrollably evacuated in an undergarment and pants. The present invention can be made independent of the undergarment or may be integrally incorporated in the undergarment.

2. Description of the Prior Art

For many male adults, young and old, urinary incontinence is a very sensitive yet serious problem. Generally, incontinence is the inability of a person to control their bladder or bowel functions. More particularly, there is a serious problem of male penile urinary incontinence. Penile incontinence is very troublesome since the glands penis, when flaccid, allows urine to flow under gravity from the bladder through the prostatic urethra, the membranous urethra and the penile urethra into an undergarment and pants resulting in visual wetting. This means that urine is continuously dripping into the undergarment of the incontinent male. Laughing, sneezing and coughing greatly exacerbate the problems associated with urinary incontinence.

Urinary incontinence can result from old age, prostate or bladder surgery, spinal cord injuries, as well as diseases such as priapism and Pyronie's. No matter what the cause of the urinary incontinence, several differing techniques have been developed to either correct or ameliorate the symptoms resulting from penile incontinence.

Some urinary incontinence may be corrected using surgical techniques. Surgical techniques include the plication of the bulbocavernosus muscle; the Marshall-Marchetti technique for women; and sling techniques such as the Cooney and Horton technique for males where two strips of fascia are cut from the aponeurosis and are freed from the rectus fibers and positioned over the pubis and under the bulb of the urethra through a tunnel and tensioned to create a restriction in the urethra.

For males who may not have elective surgery possibly due to health complications or old age, and for those males where the urinary incontinence cannot be surgically corrected, there are very few options. If surgery is not an option for an adult incontinent, then there only remains the use of adult diapers to soak up the discharging urine. However, diapers are very annoying, costly, unsightly and obtrusive. For an active person, diapers are a nuisance. For any adult, having to wear a diaper can be unpleasant and embarrassing.

Diapers are also very undesirable because they are unsanitary. Despite significant research and development, diapers still allow the excreted fluid to remain in contact with the skin until a new diaper is applied. However, this is a serious problem for an incontinent person who is continuously excreting small amounts of urine. It would be necessary to continuously change the diaper to avoid rashes and skin irritations completely.

Some attempts have been made to minimize the problems associated with changing the diaper of an incontinent male. For example, U.S. Pat. No. 5,074,853, to Bryant, discloses a male incontinent diaper that is designed to minimize the exposure to wetness by not having adjacent body portions come in contact with the wet diaper. Accordingly, the diaper covers only the end of the penis and is secured to the shaft. Similar to the Bryant patent is U.S. Pat. No. 4,601,716, to Smith that also discloses a penis diaper.

The problem with these devices is that they allow the penis to continue to drip urine that will continue to contact the skin and cause rashes and irritation. Therefore there will necessarily be contact with a wet diaper.

It is also known in the prior art to use both inner and external catheters connected to bags for collecting the urine. Examples of these types of devices are shown in the products offered by ConvaTec, a Bristol Myers Squibb Company. This information is available via the internet at http://www.convatec.com. However, catheters, internal and external, as well as their appended baggage are sightly and troublesome. Furthermore, catheters are very constrictive and do not allow the wearer an active life style.

It should also be noted that it is possible to simply supply a "pinching" device which closes the urethral passage. A primitive example of this type of device is the human hand pinching the penis between the forefinger and the thumb. However, this is not very useful to an active person. A slight improvement over the human hand is the URO Flow Control device available from FDC, Inc. and shown on the internet at http://www.flashdistributor.com/uroflow.html. The URO Flow device is essentially a simple, plastic, u-shaped ring having a threaded screw and press plate. The u-shaped section is placed around the penis and a flat portion closes the legs of the u-shaped section. The press plate moves into the bight portion of the u-shaped section of the device via the threaded screw connected to the flat portion.

The URO Flow device has many drawbacks and potential safety problems. If the URO Flow device is tightened too much, circulation of blood within the penis can be unduly restricted. Furthermore, the URO Flow device does not allow for changing penis sizes in the event of arousal or thermal changes. Finally, the URO Flow device must be made with different size u-shaped sections to accommodate different size males. This adds significant cost to the product due to additional capital being required.

Accordingly, the prior art is lacking in many respects. In particular, the prior art nowhere discloses or teaches a device that will prevent the discharge of urine by occluding the urethra, without penile damage, in an incontinent male. Furthermore, the prior art nowhere discloses a device that can be used by an incontinent male who is active in sports and other endeavors. The prior art does not disclose or teach a device that is not sightly or complicated in its solution to the problem of urinary incontinence.

SUMMARY OF THE INVENTION

The present invention includes a urethral occluder, that may be incorporated into an undergarment, for occluding the penis of an incontinent male to prevent urine from being uncontrollably voided. More particularly, the present invention includes a urethral occluder and penile positioner that will position the penis to counter the effects of gravity and occlude the urethra to prevent urine from being uncontrollably voided. Further, the present invention includes a urethral occluder and penile positioner integrally incorporated into an undergarment for occluding and positioning the penis of a male wearing the garment. A person wearing the urinary incontinence device according to the present invention can assuredly partake in physical activities without worrying about wetting their undergarment and the visual indica associated therewith, and without worrying about changing a diaper.

The urethral occluder of the present invention is integrally incorporated into an undergarment having an exterior flap covering a hole aligned with the base of the penis when the undergarment is worn. The penis passes through the hole in the undergarment such that the hole of the undergarment rests at the base of the penis. The penis is vertically positioned and the exterior flap is placed over the penis so the occluder, incorporated in the flap, is positioned aligned with the base of the penis and the urethra. The flap is designed to stretch and move either vertically, i.e., from bottom to top, or horizontally, i.e., from side to side. The flap is preferably made of a smooth material that stretches tightly over the penis to keep the penis properly positioned and the occluder pressed relatively tightly against the base of the penis such that the urethra is occluded.

The occluder incorporated into the flap is preferably made of a relatively hard rubber material that is pliable yet firm. Additionally, the occluder includes a relatively harder insert to provide the occluder additional rigidity. The insert may be made of any material such as metal, alloy, plastic or rubber.

The urinary incontinence device of the present invention may be incorporated into nearly any type of undergarment. For example a pair of briefs can made to include an opening and a flap having the occluder, according to the present invention. Similarly, a pair of boxer shorts, a jockstrap or even a "g"-string or a sling can be designed to be combined with the occluder of the present invention thereby allowing the incontinent male to have significant freedom in the type and style of dress.

The present invention also encompasses embodiments where the occluder is separate from the undergarment. The occluder is attached to the penis using other attachment means such as a stretchable wrap, a band strap having self adhesive properties or other similar structure. The occluder is made integral with the strap and is again positioned to be located at the base of the penis to occlude the urethral passage. In this embodiment it is advantageous to include a dorsal vein protector to prevent circulation or blood within the penis from being unduly limited.

In all of the above mentioned embodiments, it is further possible to include an occluder that can be enlarged using an expandable chamber located within the occluder and a means for expanding the chamber, such as an air pump or similar device. In the pump embodiment, the occluder is located in its normal manner and then the occluder is pumped to expand the occluder and provide occlusion of the urethral passage.

Accordingly, it is an object of the present invention to provide a device that will provide a male person with the ability to counter the visible physical affects of urinary incontinence, primarily, the wetting of undergarments and pants and resulting skin irritation.

It is a further object of the present invention to provide a urinary incontinence device incorporated in an undergarment that is comfortable to wear and allows physical activity and eliminates the need for diapers of any type.

It is yet a further object of the present invention to provide a urinary incontinence device that will safely maintain the position of the penis and occlude the urethral passage.

It is yet a further object of the present invention to provide an undergarment urinary incontinence device that will safely occlude the urethral passage without damage to the penis and will protect the venous outflow of the penis.

It is yet a further object of the present invention to provide an occluding device for occluding the urethral passage that can be used in conjunction with or separately from an undergarment.

It is a further object of the present invention to provide an urethral passage occluding device including an expandable occlusion device.

It is a further object of the present invention to provide an urethral passage occluding device wherein the expandable occlusion device includes an expandable chamber located in the occlusion device and a pump for expanding the occlusion device.

These and other objects of the present invention will become apparent from the following detailed description of the preferred embodiment taken in conjunction with the attached drawings which are briefly described as follows.

DETAILED DESCRIPTION OF THE PREFERRED EMBODIMENT

Figure 1:
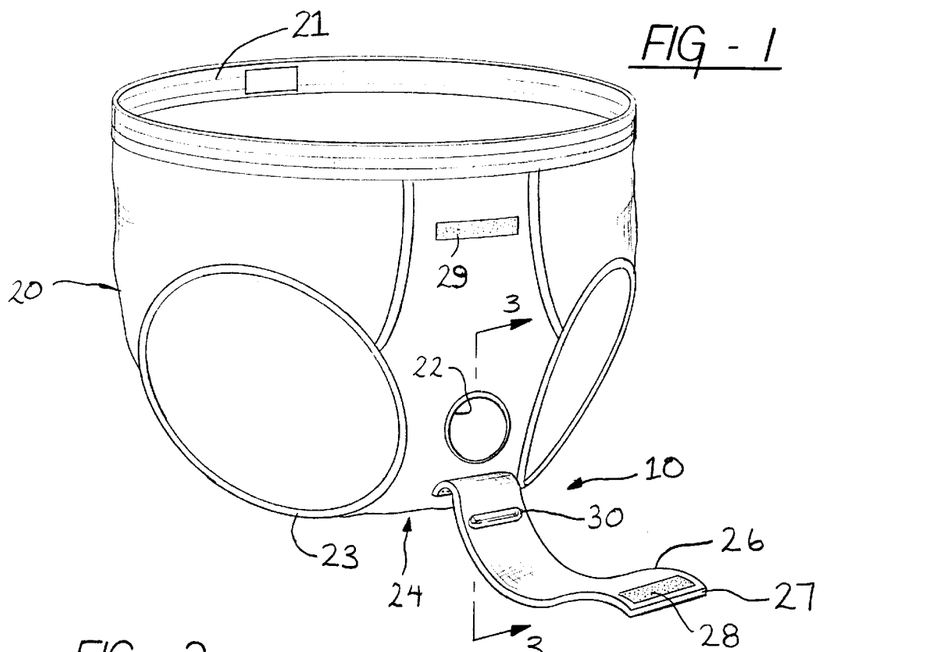
FIG. 1 is a perspective view of a preferred embodiment of an urinary incontinence device for positioning and occluding the penis according to the present invention.
Figure 2:
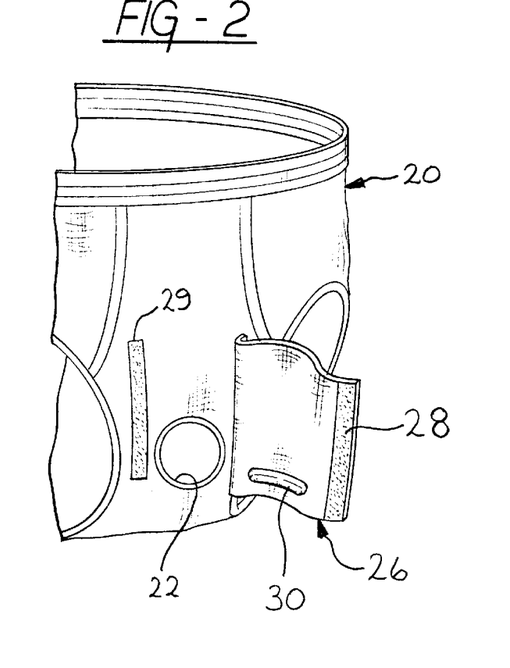
FIG. 2 is a perspective view of an alternate embodiment of an urinary incontinence device for positioning and occluding the penis according to the present invention.
Figure 3:
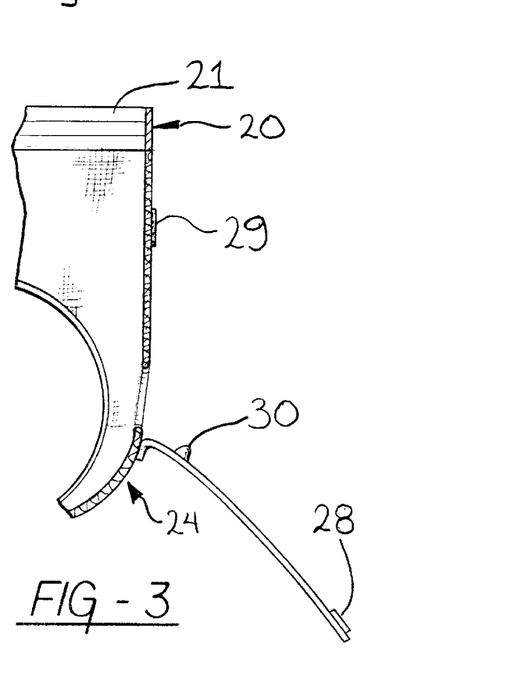
FIG. 3 is a detail section taken along the line 3—3 in FIG. 1 detailing the flap connection of the preferred embodiment according to the present invention.

Referring generally to FIG. 1 through FIG. 3 and particularly to FIG. 1 through FIG. 5, an urinary incontinence device 10 for completely preventing a male urinary incontinent from wetting his undergarment and pants is shown. The urinary incontinence device 10 in the preferred embodiment includes an undergarment 20 having a waistband 21 and a pair of leg openings 23, as is well known in the undergarment art. The undergarment 20 further includes an opening or a hole 22 located in a front portion 24 thereof. The hole 22 is located within the front portion 24 so when the undergarment 20 is worn, the shaft of the wearer's penis will easily extend through the hole 22 and can then be positioned vertically upward against the torso. Because the undergarment 20 is preferably made of a stretchable material, as described below, the hole 22 will accommodate nearly any size penis.

A flap 26 is sewn to the front portion 24 preferably beneath the hole 22 and is designed to move vertically. The flap 26 has an end 27 having a fastening strip 28 located thereon. The undergarment 20, of the preferred embodiment, has a second fastening strip 29 attached to the undergarment 20 at a point above the hole 22 and is removably attachable with the fastening strip 28. The fastening strip 28 is preferably made of any material that is removably attachable, such as a hook and loop material such as Velcro® brand fastening material. However, it should be appreciated that any appropriate type of fastening means may be used such as a snap, a clasp, a button or any other closure member.

Figure 4:
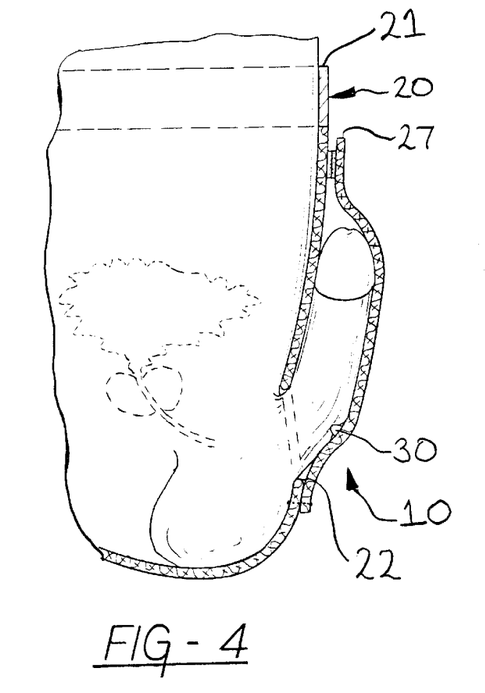
FIG. 4 is a cross section view of the urinary incontinence device according to the present invention while being worn.

The flap 26 moves vertically to position and maintain the penis of the wearer in a vertical position to offset the effects of gravity upon the wearer. As the flap 26 is moved vertically, the shaft of the penis is lifted and an occluder 30 located thereon is automatically located at the shaft of the penis. It should be noted that since only the shaft of the penis extends though the hole 22, the scrotum of the wearer is protected and does not affect the operation of the urinary incontinence device 10 of the present invention, as best shown in FIG. 4 wherein the urinary incontinence device 10 of the present invention is shown with the flap 26 closed and the shaft of the penis occluded by the occluder 30.

The undergarment 20 may be made of any known material but is preferably made to be form fitting to the body of the male such as with men's brief undergarments. Accordingly, it is preferable to make the undergarment out of cotton, Spandex® or Lycra® material. Similarly, the flap 26 is also made of a stretchable and elastic material. It should be understood that it is also possible to have the undergarment made of one type of material and the flap 26 made of a different material.

As described above, the flap 26 has incorporated therein the occluder 30. The occluder 30 is preferably made of a semi-hard rubber material. The occluder 30 may alternatively have a metal, alloy or plastic middle insert enclosed by the semi-hard rubber material such that the insert will provide additional support and effectiveness to the occluder 30.

The occluder 30 is incorporated within the flap 26 at a point aligned with the hole 22 in the undergarment 20 such that when the flap 26 is vertically positioned to have the fastening strip 28 connected to the second fastening strip 29, the occluder 30 will be located at the base of the shaft of the penis and will press thereagainst to occlude the urethral passage of the penis and prevent urine from being uncontrollably voided.

In an alternate embodiment, as shown in FIG. 2, it is possible to have a flap 26 that is designed to move in a horizontal direction as opposed to the vertically moving flap 26 as shown in the embodiment of FIG. 1. The horizontally moving flap 26 of FIG. 2 still includes the occluder 30 positioned with respect to the hole 22 in the front portion 24 of the undergarment 20. In the embodiment of FIG. 2, the wearer of the undergarment 20 will manually position the shaft of the penis in a vertical position and then move the flap 26 horizontally to position the occluder 30 at the base of the penis extending through the hole 22.

Figures 6, 7:
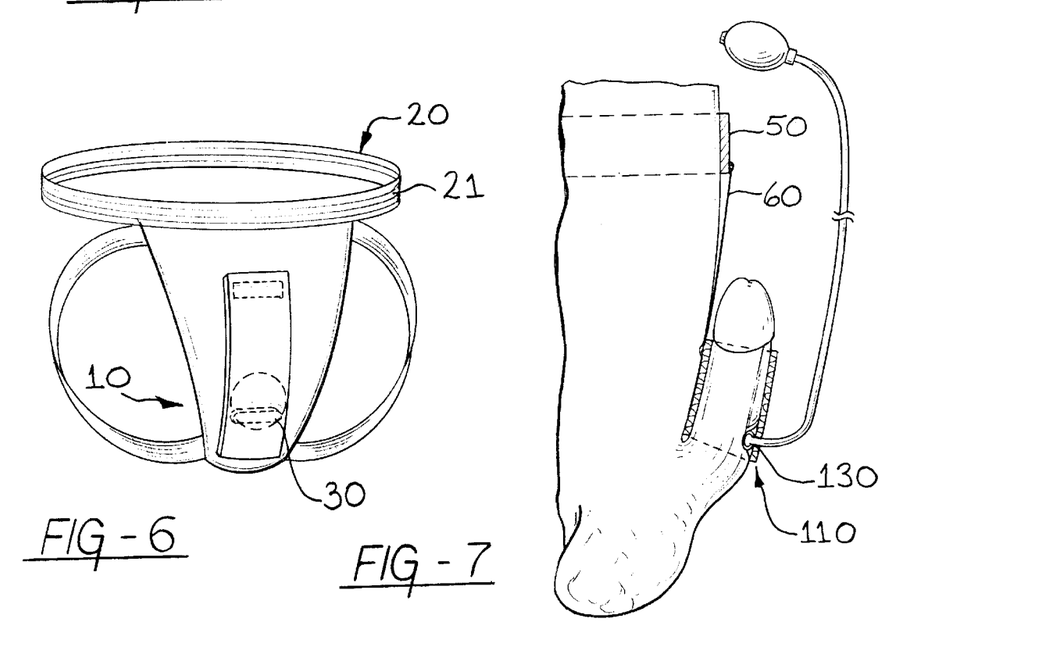
FIG. 6 is a plan view of an alternate embodiment of the urinary incontinence device of the present invention incorporated in a jock strap.
FIG. 7 is a partial breakaway side view of an alternate embodiment of the urinary incontinence device of the present invention shown separately from an undergarment and incorporating an inflatable bladder.

It should be appreciated form the above that the urinary incontinence device 10 of the present invention can be incorporated into nearly any style or design of undergarment 20. For example, with appropriate design and manufacturing considerations addressed, the urinary incontinence device 10 can be incorporated into any style cotton brief, jock strap or similar undergarment 20, for example, as shown in FIG. 6. Furthermore, the urinary incontinence device 10 can also be incorporated into any style boxer short by having the brief sewn into the boxer short similar to a bathing suit, which can also have the present invention incorporated therein.

Figure 5:
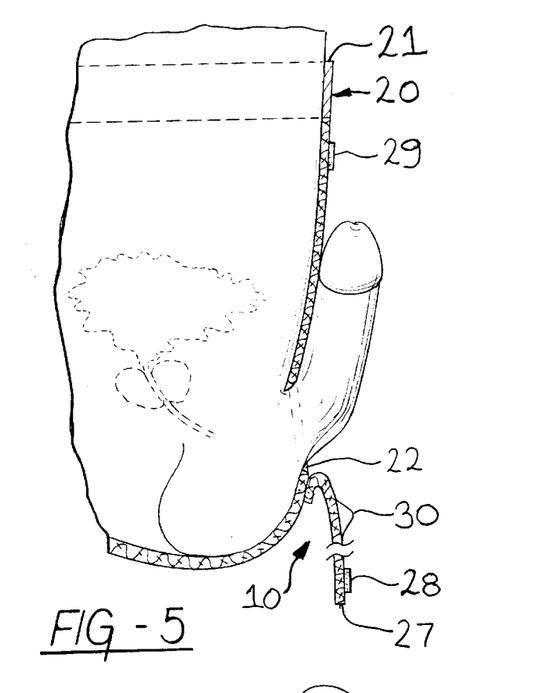
FIG. 5 further details the process of using the urinary incontinence device of the preferred embodiment according to the present invention as it is intended to be worn.

It should be understood that the undergarment 20 of the preferred embodiment shown in FIG. 1 and FIG. 3 necessarily has associated therewith a unique method of use. Starting with FIG. 5, there is shown the wearer first donning the undergarment 20 having the urinary incontinence device 10 according to the present invention. The wearer inserts the penis through the hole 22 of the undergarment 20 such that the penis extends completely therethrough, the scrotum does not pass through the hole 22 and the hole 22 is aligned with the base of the shaft of the penis, as best shown in FIG. 5. Next, the flap 26 is moved, vertically as shown in FIG. 4 and FIG. 5, or horizontally as shown in FIG. 2, and either prior or simultaneously, the penis is lifted vertically. Then the end 27 of the flap 26 having the fastening strip 28 is secured to the second fastening strip 29.

Simultaneously with the flap being moved, or prior thereto, it is possible for the wearer to manually lift the penis and place it in a vertical position along the wearer's abdominal area. Similarly, the occluder 30 can also be manually positioned at the base of the penis to ensure comfort and occlusion of the urethral passage.

Once the flap 26 is closed and the occluder 30 positioned, the wearer is set to engage in nearly any normal activity. When the wearer determines it is appropriate to void, based upon either a preset time or upon the feeling of pressure, the wearer goes to the bathroom. First the wearer ensures the occluder 30 maintains the urethral passage occluded and the penis remains vertical to counter the effects of gravity and then the flap 26 is unsecured and moved down or aside as appropriate. The wearer then aims appropriately and allows the occluder 30 to cease occluding the urethral passage thereby voiding the urine which has built up in the wearer's system.

Figures 8, 9, 10, 11:
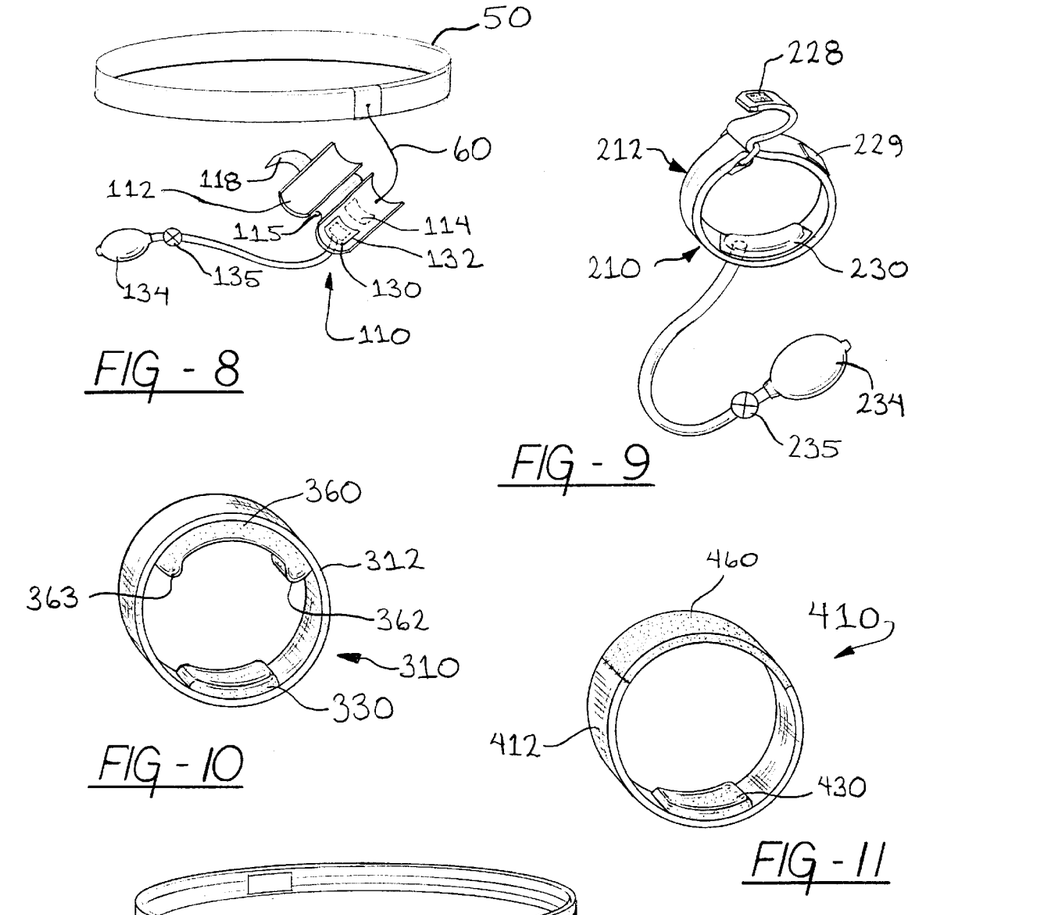
FIG. 8 is perspective view of a further alternate embodiment of the urinary incontinence device of the present invention wherein the device includes a pair of half-rounded members and an inflatable occlusion device.
FIG. 9 is a side view of a further alternate embodiment of the urinary incontinence device of the present invention including a self adhering strap and an inflatable occlusion device.
FIG. 10 is a side view of a further alternate embodiment of the urinary incontinence device of the present invention utilizing an elastic band, an occluder and a dorsal vein protection device.
FIG. 11 is a side view of a further alternate embodiment of the urinary incontinence device according to the present invention including an elastic band having a partial rigid section aligned with the dorsal veins of the penis and an occlusion device according to the present invention.

An alternative of the urinary incontinence device 10 to that of the preferred embodiment is shown in FIG. 7 and FIG. 8, wherein there is shown an urinary incontinence device 110. The present device 110 is not designed to be made integral with an undergarment but instead utilizes a belt 50 and connection strap 60 to help ensure the device 110 is positioned and remains in a substantially vertical position. Additionally the device 110 is designed differently than the device 10 in that a substantially rigid material, such as plastic is used to make a first half 112 and a second half 114 connected by a hinge 115 that are used to encompass the penis of the wearer.

Furthermore, the occluder 130 of the device 110 is made of a bladder 132, a pump 134 and a valve 135. The occluder 130 is located on the second half 114 at one end thereof such that when the device 110 encompasses the penis of the wearer, the occluder 130 will be located at the base of the shaft of the penis.

The first half 112 is designed to overlap the second half 114 in such fashion that the penis will not be caught yet will provide for differing sizes. A closure strap 118 is provided for connecting the first half 112 to the second half 114. The closure strap 118 may use any known closure means similar to the fastening strips 28 and 29 of the embodiment of FIG. 1. Thus, when the first half 112 is closed to the second half and the penis is encompassed, as best shown in FIG. 7, the occluder 130 is pumped up so the bladder 132 places additional pressure to close the urethral passage of the wearer. The semi-rigid design of the first and second halves prevents the flow of blood in the penis from being unduly constricted by the pressure applied by the occluder 130.

The device 110 is provided with the belt 50 connected to the end opposite the occluder 130 by the strap 60 such that once the device 110 is applied, the wearer can maintain the device in a substantially vertical position. The strap 60 is adjustable to allow for the proper amount of lift depending upon size and comfort.

Additional alternative embodiments of the device 110 of FIG. 7 and FIG. 8 are shown in FIG. 9 through FIG. 11. For example, FIG. 9 shows an urinary incontinence device 210 similar to FIG. 8 but wherein the first and second halves 112 and 114, respectively, are replaced using a strap 212 having a self adhering closure material 228 and 229 similar to the flap 26 of the device 10. Thus, the device 210 is very compact and lightweight. The device 210 is similarly provided with an occluder 230 having a bladder 232 a pump 234 and check valve 235 similar to the device 110.

It should be understood that the pump having a one-way check valve, the hose, the valve and the bladder of the present invention can be of nearly any type appropriate for the particular application. In particular, it is possible for the valve 135 to be located such that the hose and pump 134 are removably attachable to the bladder 132 of the occluder 130. Additionally, while not suggestive of the present invention, any pump, bladder and valve similar to those known in the shoe art may be used in the present invention.

In yet a further alternate embodiment, an urinary incontinence device 310 is shown in FIG. 10 wherein the device 310 includes an elastic strap 312. The elastic strap 312 is preferably made of a stretchable wrap material similar to that used in ace bandages, that is a breathable, stretchable, elastic gauze material, that is preferably hypoallergenic.

The device 310 further includes, in the present embodiment, a dorsal vein protector 360, in the form of a semi-hard rubber material located on one side of the strap 312. The protector 360 extends the width of the strap 312 and extends a portion of the circumference of the strap 312. The protector 360 includes a recessed portion 362 that is to be aligned with the dorsal side of the penis above the dorsal vein such that extensions 363 and 364 of the protector contact the penis and the recessed portion 362 does not contact the penis or at least contact the penis with very low pressure so as to not cut off the flow of blood within the dorsal vein.

The device 310 of the present invention further includes an occluder 330 similar to the occluder 30 of the device 10. However, it is entirely possible for the device 310 of the present embodiment to include the pump-style occluder 130 of the device 110 in combination with the protector 360. Furthermore, it is also possible to include the belt 50 and adjustable strap 60 of the device 110 with the device 310 of the present embodiment as an aid in positioning and maintaining the penis in a substantially vertical position aligned with the torso of the wearer. However, with the device 310 it is most preferable that the wearer use the device 310 while wearing a form fitting undergarment (not shown in FIG. 10) similar to the undergarment 20 of the device 10 shown in FIG. 1.

The embodiment of FIG. 10 can be varied to be a device 410 including a dorsal vein protector 460, as shown in FIG. 11, that forms an integral part of the strap 412, instead of being merely attached, as is the case for the strap 312 in the embodiment shown in FIG. 10. Again, the strap 412 is preferably made of an elastic gauze material as in the device 310 and the protector 460 is made of a substantially inelastic, semi-hard, pliable material, such as a relatively stiff foam rubber, or other similar material that protects the dorsal vein of the penis and prevents undue constriction thereof. The occluder 430 of the present embodiment is similar to the occluder 330 of FIG. 10.

Figure 12:
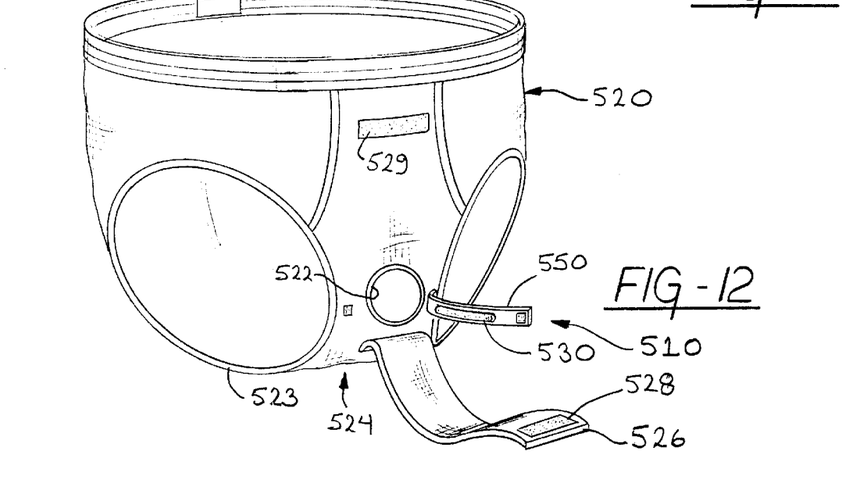
FIG. 12 is a perspective view of a further alternate embodiment of a urinary incontinence device for positioning and occluding the penis according to the present invention wherein the occluder functions separately from the positioner.

FIG. 12 shows a device 510 for occluding and positioning the penis which is a further alternate embodiment similar to the device 10 of FIG. 1. However, the device 510 has an occluder 530 that is connected to a flap 550 which is essentially a thin strip of undergarment material flapping in a horizontal direction. The flap 550 is secured to the undergarment 520 using the known fastening materials. The flap 550 is located with respect to the 522, which is essentially identical to the hole 22 of the device 10, such that the occluder 530 will close the urethral passage once a penis is positioned through the hole 522 and the flap 550 is secured thereacross.

Once the flap 550 is secured in place, a flap 526 of the device 510 is moved vertically to position the penis against the torso vertically similar to the device 10 of FIG. 1. Because in the embodiment of the device 510, the occlusion and positioning functions are separated in distinct structures, it is possible to substitute different structure for each item. For example, it is possible to use the device 310 of FIG. 10 to occlude the urethral passage with the flap 526 moving in a vertical direction to position the penis.

Figure 13:
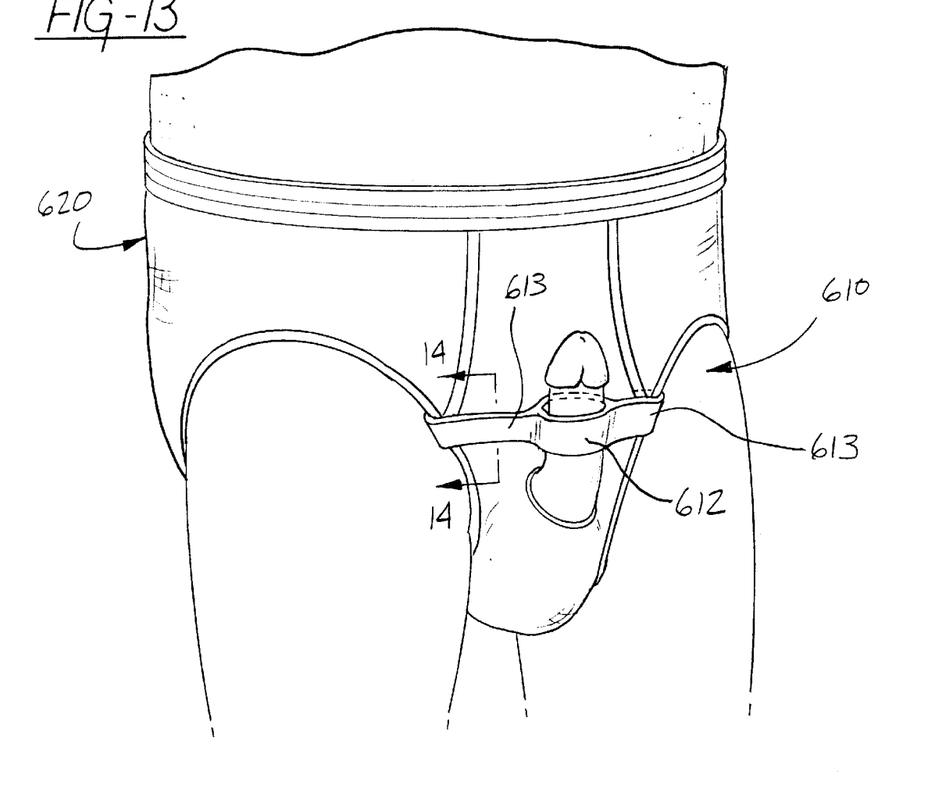
FIG. 13 is a perspective view of a further alternate embodiment of a urinary incontinence device for positioning and occluding the penis according to the present wherein an alternate connection apparatus is detailed.
Figure 14:
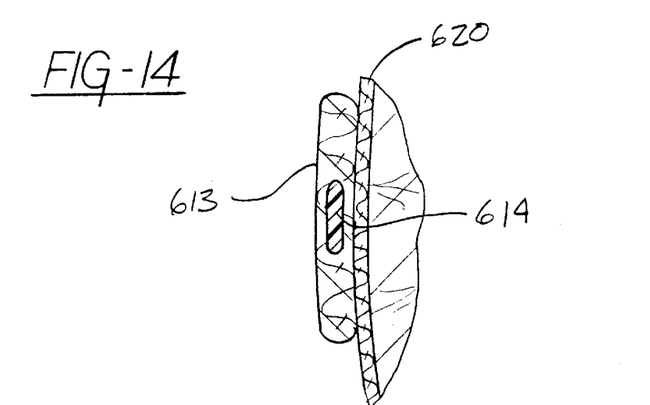
FIG. 14 is a cross-section of the device of FIG. 13.

In a further alternate embodiment, as shown in FIGS. 13, and 14, there is shown a urinary incontinence device 610 for positioning and occluding a urethral passage of a penis, as shown. The device 610 includes a ring portion 612 encircling a portion of the shaft of the penis. The ring portion 612 is preferably made of an elastic or stretchable material similar to the devices 310 and 410, or as a band similar to the device 210.

The ring portion 612 includes a pair of wings 613, which extend from the ring portion 612 at substantially opposite sides thereof. Each wing portion 613 preferably includes a soft cotton cloth on the outside, a thin layer of padding underneath the cotton cloth and an inner, pliable member 614. The pliable member 614 is preferably made of a bendable metal or alloy that is capable of maintaining a set position once the wing portions 613 are wrapped around the leg openings of the undergarmet 620.

The device 610 of the present embodiment is particularly useful since it can be manufactured at a minimum of cost and sold as a disposable incontinence device. This is very beneficial for sanitary purposes.

In a further alternate embodiment, the device 310 is attached to the penis and is then attached directly to the undergarment 520 using any known attaching means such as the Velcro® used in other embodiments or items such as a button, pin, clip or any other type of attaching or connecting device. Thus, the device 310 provides the occluding function and the positioning function at the same time. It should be understood by a person of ordinary skill in the art to which the invention pertains that the device 310 may be attached to the undergarment in any fashion and also may be used in conjunction with the flap 526.

Based upon the above, the urinary incontinence devices of the present invention will provide a wearer substantial protection against uncontrollable voiding of urine into the undergarment and pants, particularly associated with incontinence. The present invention provides both occlusion and positioning of the penis to prevent uncontrollable urine discharge. Since the present invention prevents the problem of wetting, it thereby avoids the necessity for diapers of any type resulting in a substantial cost savings and avoidance of problems associated with diapers. Furthermore, the present invention can be made very compact, making it very discreet, and is reusable, washable and designed to be hypoallergenic. The present invention exists in many different embodiments.

Accordingly, the invention is not limited to the embodiments described and shown in the accompanying drawings and description. It is understood that modifications are possible, particularly with respect to the type of undergarment, the shape of the flap and other design configurations that are simple modifications of the invention. For example, it is possible to provide an occluder made of different material or attached using different structure. The above embodiments of the present invention are to be considered illustrative and not restrictive when taken in conjunction with the appended claims.

What is claimed is:

1. An urinary incontinence device for positioning a penis and occluding a urethral passage of the penis to prevent urine from uncontrollably passing therethrough, said device comprising:
    (a) an undergarment having a pair of leg openings for being worn by a person, the undergarment having a hole located in a front portion of the undergarment for receiving the penis therethrough;
    (b) a flap having a first end attached to the undergarment and located with respect to the hole, the flap having a second end detachably connected to the undergarment; and
    (c) an occluder incorporated in the flap and located with respect to the hole of the undergarment for applying pressure to the penis.

2. The urinary incontinence device according to claim 1 wherein the flap is attached to the undergarment at a point below the hole and the flap moves vertically to position the penis against the body.

3. The urinary incontinence device according to claim 1 wherein the flap is attached to the undergarment at a point along a side of the hole and the flap moves horizontally to position the penis against the torso of the body.

4. The urinary incontinence device according to claim 1 wherein the flap is attached to the undergarment at a point above the hole and the flap moves vertically to position the penis against the torso of the body.

5. The urinary incontinence device according to claim 1 wherein the occluder comprises a semi-hard material having a relatively harder insert.

6. A method for positioning a penis and occluding a urethral passage of the penis for preventing urine from uncontrollably being voided from the bladder, said method comprising the steps of:
    (a) donning an undergarment having a pair of leg openings and a front portion, the front portion including a hole, the undergarment including a flap connected thereto, the flap having a first end connected to the undergarment and a second end removably attachable to the undergarment and an occluder;
    (b) positioning the penis within the hole of the undergarment such that the penis extends through the hole;
    (c) moving the flap to position the penis vertically next to the body of the wearer;
    (d) locating the occluder at the base of the penis to occlude the urethral passage of the penis; and
    (e) attaching the second end of the flap to the undergarment whereby the occluder presses against and occludes the urethral passage of the penis and locates the penis in a relatively upright position aligned with the torso of the body to prevent urine from being uncontrollably voided.

7. An urinary incontinence device for preventing urine from being uncontrollably voided into the wearer's garments, the urinary incontinence device comprising:
    (a) an enclosure for surrounding at least a portion of the penis including the base of the penis, the enclosure including a first member and a second member hinged to the first member;
    (b) a closure strap for securing the first member to the second member in a closed position around the penis;
    (c) an occluder connected to the first member at one end thereof for alignment with the base of the penis proximate the urethral passage;
    (d) an adjustable belt to be worn about the waist of the wearer of the urinary incontinence device; and
    (e) an adjustable strap having a first end connected to the belt and a second end connected to the enclosure at an end opposite the occluder, the adjustable strap and belt for positioning the penis in a position aligned with the torso of the wearer such that the penis is substantially vertical when the wearer is standing.

8. The urinary incontinence device of claim 7 wherein the occluder is made of a relatively elastic, stretchable material, the occluder comprising:
    (a) a bladder located within the occluder for receiving a fluid;
    (b) a hose having a first end and a second end, the first end connected to the bladder, the hose for conveying fluid into the bladder;
    (c) a pump for pumping a fluid into the bladder, the pump connected to the second end of the hose and including a one-way check valve; and
    (d) a valve connected to the occluder, the valve for retaining fluid within the bladder and for selectively allowing fluid to exit the bladder.

9. The urinary incontinence device of claim 8 wherein the hose and pump are removably attached to the bladder of the occluder.

10. The urinary incontinence device of claim 7 wherein the enclosure is made from a plastic material and the occluder includes a bladder located therein.

11. The urinary incontinence device of claim 7 further comprising a dorsal vein protector connected to the enclosure for preventing blood flow in the dorsal vein of the penis from being blocked.

12. An urinary incontinence device for preventing urine from being uncontrollably voided into the wearer's garments, the urinary incontinence device comprising:
   (a) an elastic strap having a substantially ring shape for surrounding at least a portion of the penis including the base of the penis;
   (b) an occluder connected to the strap at a first point for alignment with the base of the penis proximate the urethral passage; and
   (c) a dorsal vein protector connected to the strap at a second point approximately opposite the occluder, the dorsal vein protector for preventing blood flow in the dorsal vein of the penis from being blocked.

13. The urinary incontinence device of claim 12 further comprising:
   (a) an adjustable belt to be worn about the waist of the wearer of the urinary incontinence device; and
   (b) an adjustable strap having a first end connected to the belt and a second end connected to the strap at a third point proximate the dorsal vein protector, the adjustable strap and belt for positioning the penis in a position aligned with the torso of the wearer such that the penis is substantially vertical when the wearer is standing.

14. The urinary incontinence device of claim 12 wherein the dorsal vein protector extends for a portion of the circumference of the elastic strap, the dorsal vein protector includes a first end having an extension, a second end circumferentially opposite the first end having an extension, the extensions of the first and second ends defining a recess therebetween such that the recess is aligned with the dorsal vein of the penis.

15. An urinary incontinence device for preventing urine from being uncontrollably voided into the wearer's garments, the urinary incontinence device comprising:
   (a) a strap having a substantially ring shape for surrounding at least a portion of the penis including the base of the penis, a portion of the strap being made of an elastic material and a portion of the strap being made of a substantially inelastic pliable material and defining a dorsal vein protector;
   (b) an occluder connected to the strap at a first point for alignment with the base of the penis proximate the urethral passage; and
   (c) wherein the dorsal vein protector forming part of the strap is located at a second point approximately opposite the occluder, the dorsal vein protector for preventing blood flow in the dorsal vein of the penis from being blocked.

16. An urinary incontinence device for positioning a penis and occluding a urethral passage of the penis to prevent urine from uncontrollably passing therethrough, said device comprising:
   (a) an undergarment having a hole located in a front portion of the undergarment for receiving the penis therethrough;
   (b) a flap having a first end attached to the undergarment at a point located with respect to the hole, the flap having a second end detachably connected to the undergarment; and
   (c) an occluder attached to the undergarment at a second point with respect to the hole of the undergarment, the occluder for applying pressure to the penis to occlude the urethral passage to prevent urine from being excreted.

17. The urinary incontinence device according to claim 16 further comprising a second flap connected to the undergarment at the second point and wherein the occluder is connected to the second flap such that after the penis is inserted through the hole, the second flap is first positioned across the penis to occlude the urethral passage and then the first flap is positioned over the penis and the second flap to position the penis against the torso of the wearer.

18. A method of using a urinary incontinence device having a bladder and a means for inflating the bladder, the method comprising the steps of:

attaching the urinary incontinence device on a penis at a position on the shaft of the penis such that the bladder is aligned with the urethral passage of the penis; and inflating the bladder to occlude the urethral passage of the penis:

positioning the penis in a position wherein the penis is located against the torso of the wearer in a substantially vertical position; and maintaining the penis in position.

19. A urinary incontinence device for positioning a penis to prevent urine from uncontrollably passing therethrough, said device comprising:
   (a) an undergarment having a pair of leg openings for being worn by a person, the undergarment having an opening located in a front portion of the undergarment for receiving the penis therethrough; and
   (b) a flap having a first end attached to the undergarment and located with respect to the hole, the flap having a second end detachably connected to the undergarment, the flap being operable to position and maintain the penis of the person in a substantially vertical position wherein the penis is located against the torso of the wearer.

* * * * *